United States Patent [19]

Veretto et al.

[11] Patent Number: 5,653,941

[45] Date of Patent: Aug. 5, 1997

[54] FOOD SPOILAGE DETECTOR

[76] Inventors: Bobby Veretto, 111 Houston St., Levelland, Tex. 79336; John W. Thomas, 4001 Greenridge Rd. #201, Pittsburgh, Pa. 15234; David L. Volk, 301 Oakwood Ct., Clairton, Pa. 15025

[21] Appl. No.: 688,659

[22] Filed: Jul. 29, 1996

[51] Int. Cl.⁶ ............................................. G01N 21/00
[52] U.S. Cl. ........................ 422/58; 422/61; 436/1; 426/232
[58] Field of Search .................... 422/58, 61; 436/1, 436/164; 426/232

[56] References Cited

U.S. PATENT DOCUMENTS

| | | | |
|---|---|---|---|
| 2,485,566 | 10/1949 | Clark | 99/192 |
| 2,626,855 | 1/1953 | Hand | 422/58 |
| 3,067,015 | 12/1962 | Lawdermilt | 23/253 |
| 4,003,709 | 1/1977 | Eaton et al. | 23/253 R |
| 4,285,697 | 8/1981 | Neary | 23/230 LC |
| 4,308,028 | 12/1981 | Elkins | 422/58 |
| 5,306,466 | 4/1994 | Goldsmith | 422/58 |
| 5,439,648 | 8/1995 | Balderson et al. | 422/86 |

FOREIGN PATENT DOCUMENTS

93/09431  5/1993  WIPO .

*Primary Examiner*—Lyle A. Alexander
*Attorney, Agent, or Firm*—David L. Volk; Brendan B. Dix

[57] ABSTRACT

An enclosure includes a hollow robe disposed at a first end thereof and extending outwardly there-from. A collapsible bulb is attached to a second end of the enclosure for drawing atmosphere into the enclosure through the hollow robe when the bulb is squeezed and released. The enclosure further includes a viewing aperture. An indicating strip is disposed in the enclosure such that the strip is in environmental communication with the interior of the enclosure and viewable through the viewing aperture from outside of the enclosure. The indicating strip is configured to change in appearance when gases indicating the presence of food contamination are absorbed by the strip.

3 Claims, 3 Drawing Sheets 5,653,941

FOOD SPOILAGE DETECTOR

BACKGROUND—FIELD OF INVENTION

This invention relates to detectors, specifically to a device which detects conditions which may indicate food spoilage.

BACKGROUND—DESCRIPTION OF PRIOR ART

Every year thousands of people consume spoiled food without knowing it. The result is illness and sometimes death. Efforts have been made in the prior art to alleviate this problem by providing food spoilage indicators incorporated into, or placed inside of food packages. These indicators are intended for installation in the package by the food manufacturer. The consumer may check the indicator to see whether or not the food is spoiled before consumption.

The drawback of these prior art solutions is that they each require the indicators to be placed in the package by the manufacturer. They do not provide a way for a consumer to check for spoilage of food in a package which doesn't already have an indicator inserted within.

What is needed is a device which a consumer may use to check any packaged food product for spoilage, even packages which do not come with an indicator already packaged within.

SUMMARY

The food spoilage detector of the present invention includes an enclosure having a hollow tube disposed at a first end thereof and extending outwardly there-from. A collapsible bulb is attached to a second end of the enclosure for drawing atmosphere into the enclosure through the hollow tube when the bulb is squeezed and released. The enclosure further includes a viewing aperture. An indicating strip is disposed in the enclosure such that the strip is in environmental communication with the interior of the enclosure and viewable through the viewing aperture from outside of the enclosure. The indicating strip is configured to change in appearance when gases indicating the presence of food contamination are absorbed by the strip.

DETAILED DESCRIPTION

Figure 1:
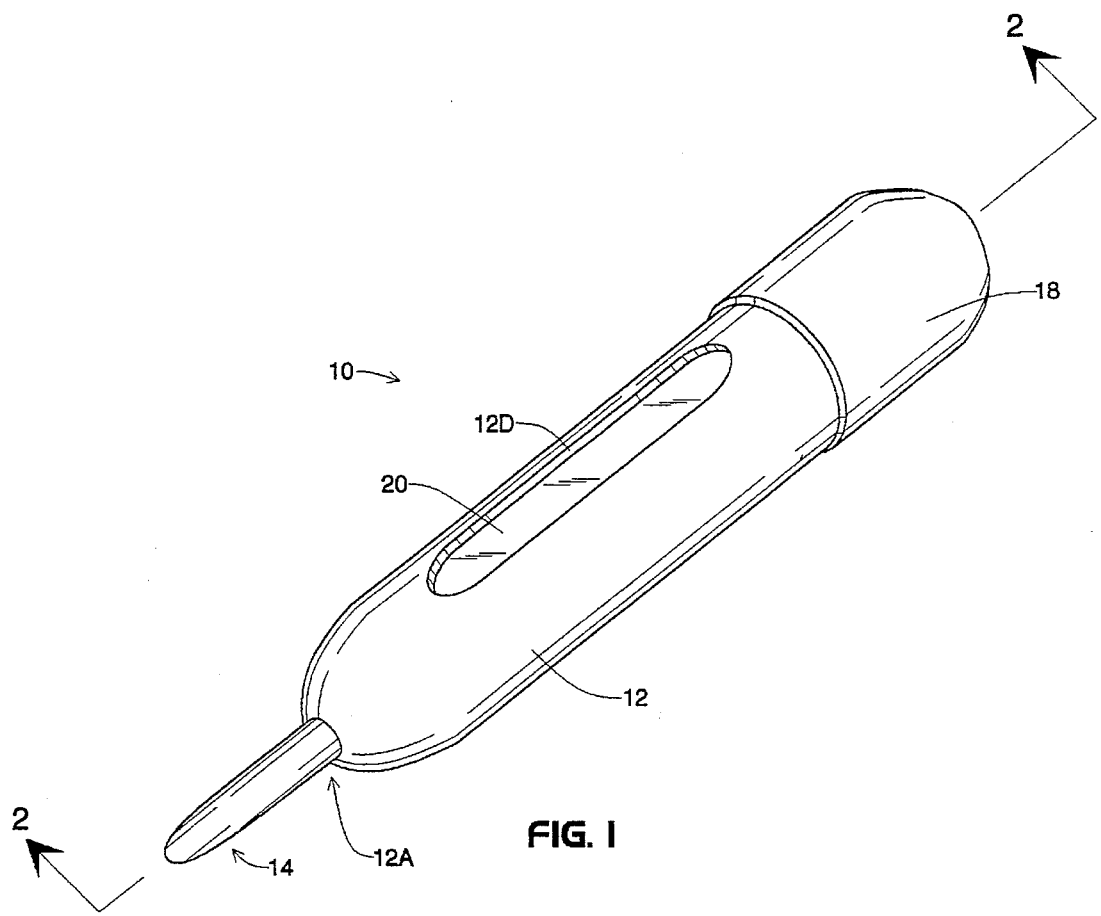
FIG. 1 is a perspective view of the food spoilage detector.
Figure 2:
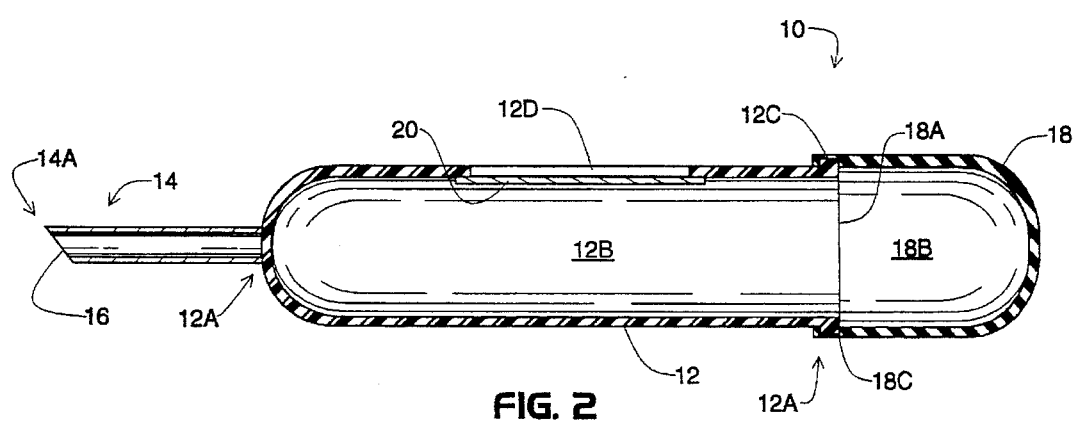
FIG. 2 is a cross-sectional view of the detector, taken along line 2—2 of FIG. 1.

FIG. 1 is a perspective view of a food spoilage detector 10. FIG. 2 is a cross-section of the indicator 10 taken along line 2—2 of FIG. 1. The detector 10 includes an elongate enclosure 12 with a hollow tube 14 disposed at a first end 12A thereof and extending outwardly there-from. The tube 14 has an angled opening 16 at its free end 14A.

The enclosure 12 includes an open second end 12A to which a collapsible bulb 18 is attached. A mouth 18A of the bulb 18 is attached to the second end 12A of the enclosure 12 such that the bulb interior 18B is in environmental communication with the enclosure interior 12B.

The bulb 18 has an annular groove 18C disposed on the interior face of the bulb 18 near the mouth 18A thereof. The second end 12A of the enclosure 12 is turned outward to form an annular lip 12C which engages the groove 18C. The bulb 18 may be further connected to the enclosure 12 by adhesive. The scope of the invention includes any type of known method of connecting the bulb 18 to the enclosure 12.

An indicating strip 20 is disposed in the enclosure 12 such that the strip 20 is in environmental communication with the enclosure interior 12B. The enclosure 12 includes structure forming a viewing aperture 12D disposed and configured such that the strip 20 may be viewed from outside of the enclosure 12 through the aperture 12D.

The indicating strip 20 changes in appearance when exposed to gases generated by food spoilage which enter the atmosphere within a package (not shown) in which the spoiled food is contained. To determine if food has been spoiled, a consumer squeezes the bulb 18, punctures the food package with the tube 14 by inserting the free end 14A into the package, then releases the bulb 18 causing some of the atmosphere inside of the package to enter the enclosure interior 12B through the tube 14. If the indicator strip 20 changes in appearance, the presence of food spoilage gases is indicated, which in turn indicates that the food is spoiled.

Figure 3:
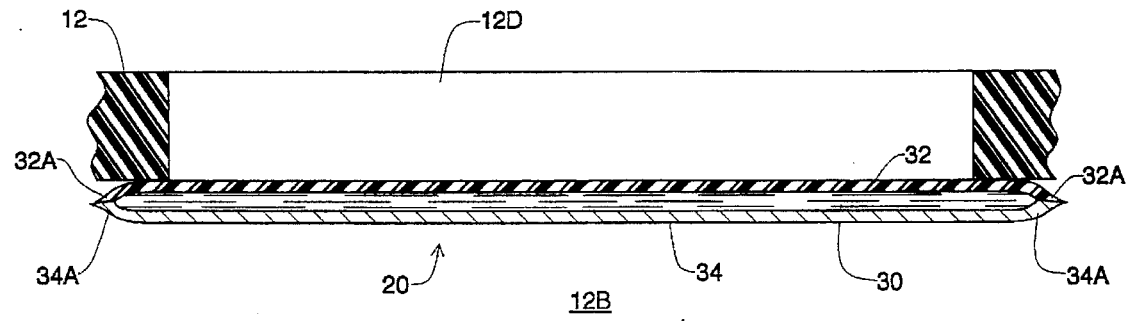
FIG. 3 is an enlarged partial cross-section of the indicating strip within the enclosure.

FIG. 3 is an enlarged partial cross-section of one embodiment of the indicating strip 20, which is disclosed in U.S. Pat. No. 4,285,697 to Neary (1981). The indicating strip 20 is shown within the enclosure 12. The indicating strip 20 comprises a liquid crystal 30 captured between a plastic layer 32 and a semi-permeable membrane 34. A plastic layer perimeter edge 32A is sealed to a membrane perimeter edge 34A, thereby sealing the liquid crystal 30 between the plastic layer 32 and the membrane 34.

The indicating strip 20 is disposed in the enclosure 12 such that the semi-permeable membrane 34 is in environmental communication with the enclosure interior 12B and the plastic layer 32 is viewable through the viewing aperture 12D. When food spoilage gases are absorbed by the liquid crystal 30 through the membrane 34, the liquid crystal 30 changes in appearance, indicating that food is spoiled. The types of gases generated by food spoilage are discussed in Neary (column 1, lines 19–36). Neary discloses several possible compositions for the liquid crystal 30 (column 2, lines 20–26) and for the semi-permeable membrane 34 (column 1, line 60 through column 2, line 2).

The scope of the invention is not limited to the use of any one particular type of indicator. For example, U.S. Pat. No. 2,485,566 to Clark (1949), U.S. Pat. No. 3,067,015 to Lawdermilt (1962), U.S. Pat. No. 4,003,709 to Eaton et al. (1977), U.S. Pat. No. 5,306,466 to Goldsmith (1994), and U.S. Pat. No. 5,439,648 to Balderson et al. all disclose food spoilage indicators for use in packages, which may find application in the present invention.

Figure 4:
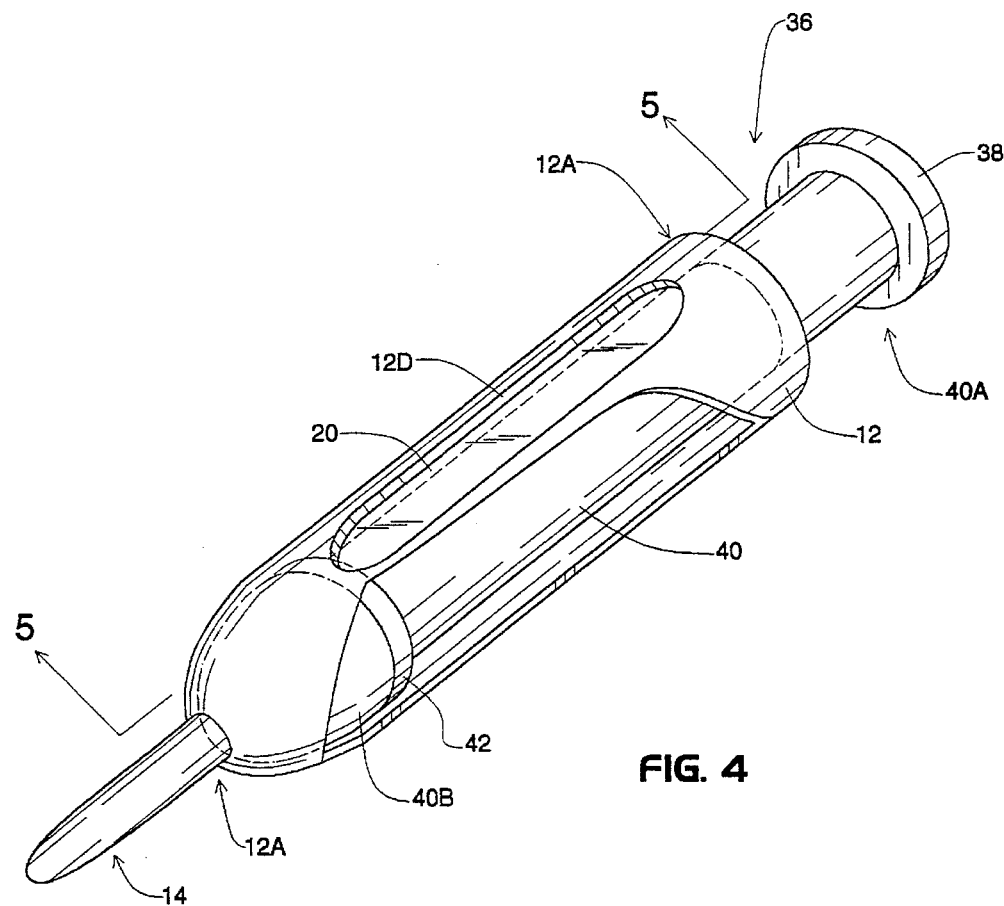
FIG. 4 is a perspective view of an alternative embodiment of the food spoilage detector, with a portion of the enclosure partially broken away to show the plunger.

FIG. 4 is a perspective view of an alternative embodiment of the food spoilage detector 10, with a portion of the enclosure 12 partially broken away to show a plunger 36. The plunger 36 includes a shaft 40 with a back end 40A and a forward end 40B. The shaft 40 extends through the second end 12A of the enclosure 12 into the enclosure 12. A handle 38 is attached to the back end 40A of the shaft 40. The forward end 40B of the shaft 40 includes a seal 42 disposed annularly about the exterior thereof. The forward end 40B and the seal 42 are configured such that the seal 42 urges outwardly against the enclosure 12. In use, the consumer punctures the food package with the tube 14 inserting the free end 14A into the package, then grips the handle 38 to pull the plunger toward the second end 12A of the enclosure 12, causing some of the atmosphere inside of the package to enter the enclosure interior 12B through the tube 14.

Figure 5:
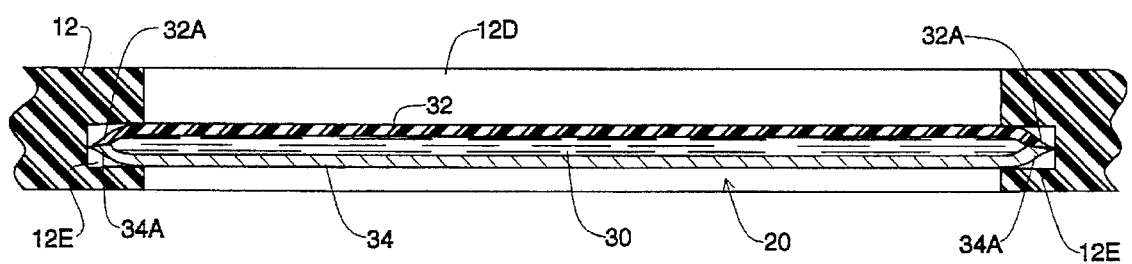
FIG. 5 is an enlarged partial cross-section taken along line 5—5 of FIG. 4.

FIG. 5 is a cross-section taken along line 5—5 of FIG. 4, showing the indicating strip 20 disposed within the viewing aperture 12D. A groove 12E is disposed within the enclosure 12 about the perimeter of the viewing aperture 12D. The sealed edges 32A, 34A of the indicating strip 20 are engaged within the groove 12E. This particular embodiment of the attachment of the strip 20 to the enclosure 12 is necessary to avoid interferences between the strip 20 and the plunger 36.

While the above description contains many specific details, these should not be construed as limitations on the scope of the invention, but rather as an exemplification of various embodiments thereof.

Accordingly, the scope of the invention should be determined not by the embodiments illustrated, but by the appended claims and their legal equivalents.

The invention claimed is:

1. A food spoilage detector comprising:
   a. an enclosure having a food spoilage indicating means disposed therein;
   b. a viewing means for viewing the indicating means from outside of the enclosure;
   c. a puncturing means attached to said enclosure for puncturing a food package; and
   d. a suction means for drawing atmosphere into the enclosure.

2. A food spoilage detector comprising:
   a. an enclosure having a hollow tube disposed at a first end thereof and extending outwardly there-from;
   b. a collapsible bulb attached to a second end of the enclosure for drawing atmosphere into the enclosure through the hollow tube when the bulb is squeezed and released;
   c. structure forming a viewing aperture in the enclosure;
   d. the enclosure further including an interior;
   e. an indicating strip disposed in the enclosure such that the strip is in environmental communication with the interior and viewable through the viewing aperture from outside of the enclosure;
   f. the indicating strip configured to change in appearance when gases indicating the presence of food contamination are absorbed by the strip.

3. A food spoilage detector comprising:
   a. an enclosure having a hollow tube disposed at a first end thereof and extending outwardly them-from;
   b. a plunger disposed within the enclosure for drawing atmosphere into the enclosure through the hollow tube when the plunger is drawn away from the first end;
   c. structure forming a viewing aperture in the enclosure;
   d. the enclosure further including an interior;
   e. an indicating strip disposed in the enclosure such that the strip is in environmental communication with the interior and viewable through the viewing aperture from outside of the enclosure;
   f. the indicating strip configured to change in appearance when gases indicating the presence of food contamination are absorbed by the strip.

\* \* \* \* \*